US012619923B2

(12) United States Patent
Pant et al.

(10) Patent No.: US 12,619,923 B2
(45) Date of Patent: May 5, 2026

(54) ENGAGEMENT LEARNING ENGINE

(71) Applicant: INVENTURUS KNOWLEDGE SOLUTIONS, INC., New York, NY (US)

(72) Inventors: Mayank Pant, New York, NY (US); Dhruv Rastogi, New York, NY (US); Shraddha Sayani, New York, NY (US); Dor Shlenger, Sebastopol, CA (US); Emil Georgiev, Hartland, WI (US)

(73) Assignee: INVENTURUS KNOWLEDGE SOLUTIONS, INC., New York, NY (US)

( * ) Notice: Subject to any disclaimer, the term of this patent is extended or adjusted under 35 U.S.C. 154(b) by 44 days.

(21) Appl. No.: 18/440,107

(22) Filed: Feb. 13, 2024

(65) Prior Publication Data

US 2024/0273423 A1     Aug. 15, 2024

Related U.S. Application Data

(60) Provisional application No. 63/445,148, filed on Feb. 13, 2023.

(51) Int. Cl.
| | |
|---|---|
| *G06Q 10/04* | (2023.01) |
| *G16H 40/20* | (2018.01) |

(52) U.S. Cl.
CPC .............. *G06Q 10/04* (2013.01); *G16H 40/20* (2018.01)

(58) Field of Classification Search
None
See application file for complete search history.

(56) References Cited

U.S. PATENT DOCUMENTS

| | | |
|---|---|---|
| 8,635,086 B2 | 1/2014 | Blom |
| 8,721,345 B2 | 5/2014 | Dickeson et al. |

(Continued)

OTHER PUBLICATIONS

Glasgow et al., The Nudge trial pragmatic trial to enhance cardio-vascular medication adherence: study protocol for a randomized controlled trial, Glasgow et al. Trials (2021) 22:528 https://doi.org/10.1186/s13063-021-05453-9.*

(Continued)

*Primary Examiner* — David J Stoltenberg
(74) *Attorney, Agent, or Firm* — KATTEN MUCHIN ROSENMAN LLP

(57)     ABSTRACT

The engagement learning engine provides for a holistic engagement model deeply rooted in the principles of human psychology, behavioral economics and mathematical correlation after studying the behavior, attitude and preferences of patients. The attitude, awareness, willingness (AAW) framework works by first identifying root causes that are causing lack of engagement and then uses the concept of behaviorally segmented 'Nudges' to deliver predictable engagement overtime. The AAW framework is preferably delivered using an artificial intelligence (AI) and machine learning (ML) technology platform to create personalized patient experience there by further enhancing and improving patient engagement. Further, the AI/ML model has cognitive learning abilities from the identified patterns, patient interactions and other inputs there by creating a perpetual loop of delivering precise nudges based on individual behaviors, outcomes delivered, interaction and other factors.

6 Claims, 4 Drawing Sheets

(56) References Cited

U.S. PATENT DOCUMENTS

| | | | | |
|---|---|---|---|---|
| 9,536,052 | B2 | 1/2017 | Amarasingham et al. | |
| 10,360,343 | B2 | 7/2019 | Prakash et al. | |
| 10,971,269 | B2 | 4/2021 | Kartoun et al. | |
| 11,132,920 | B2 | 9/2021 | Angelopoulos et al. | |
| 11,328,820 | B2 | 5/2022 | Griffin et al. | |
| 11,382,507 | B2 | 7/2022 | Wong et al. | |
| 11,663,607 | B2 | 5/2023 | Billigmeier et al. | |
| 11,830,623 | B1 | 11/2023 | Aranke et al. | |
| 2008/0015891 | A1 | 1/2008 | Lee | |
| 2010/0280935 | A1 | 11/2010 | Fellowes et al. | |
| 2012/0197717 | A1* | 8/2012 | Rampell | G06Q 50/188 705/14.51 |
| 2012/0239560 | A1* | 9/2012 | Pourfallah | G06Q 20/102 705/40 |
| 2014/0200909 | A1* | 7/2014 | Felix | G06Q 10/10 705/2 |
| 2014/0278480 | A1* | 9/2014 | Baniameri | G16Z 99/00 705/2 |
| 2014/0372133 | A1 | 12/2014 | Austrum et al. | |
| 2015/0356275 | A1* | 12/2015 | Williams | G16H 70/20 705/2 |
| 2016/0342758 | A1* | 11/2016 | Ivanoff | G06Q 10/10 |
| 2017/0193178 | A9 | 7/2017 | Di Lascia et al. | |
| 2018/0277252 | A1* | 9/2018 | Drenkard | G16H 50/20 |
| 2019/0087543 | A1* | 3/2019 | Abou Mahmoud | G16H 50/20 |
| 2020/0327608 | A1* | 10/2020 | Chuah | G06Q 10/40 |
| 2021/0104307 | A1* | 4/2021 | Das | G16H 20/00 |
| 2021/0125695 | A1 | 4/2021 | Shor et al. | |
| 2021/0134435 | A1 | 5/2021 | Deno et al. | |
| 2021/0256490 | A1* | 8/2021 | Bain | G06Q 20/102 |
| 2022/0148730 | A1 | 5/2022 | Naumov et al. | |
| 2022/0406466 | A1 | 12/2022 | Andrews | |
| 2023/0017196 | A1* | 1/2023 | Jain | H04L 67/01 |
| 2024/0412841 | A1* | 12/2024 | Viggósson | G16H 20/60 |

OTHER PUBLICATIONS

Sant'Anna et al. Nudging healthcare professionals in clinical settings: a scoping review of the literature; Sant'Anna et al. BMC Health Services Research (2021) 21:543.*

Lin Yoong et al. Nudge strategies to improve healthcare providers' implementation of evidence based guidelines, policies and practices: a systematic review of trials included within Cochrane systematic reviews; Yoong et al. Implementation Science (2020) 15:50.*

Boyce et al. Choosing a High-Quality Hospital; The role of nudges, scorecard design and information; 2010 by The King's Fund; Charity registration No. 1126980 All rights reserved, including the right of reproduction in whole or in part in any form ISBN: 978 1 85717 603 2.*

Graffigna et al. Measuring patient engagement: development and psychometric properties of the Patient Health Engagement (PHE) Scale, Frontiers in Psychology |www. frontiersin.org Mar. 1, 2015 |vol. 6 |Article274.*

"Patient Engagement Intelligence", Millennia, Oct. 4, 2023, 7 sheets, https://millenniapay.com/recover/engagement-intelligence/.

"AI-Enhanced Billing & Software", Claimocity, Aug. 5, 2020, 4 sheets, https://claimocity.com/artificial-intelligence-medical-billing-coding/.

Mayank Pant, "Journey From Patient Outreach To Meaningful Patient Engagement: How Behavioral Economics May Help", Forbs Technology Council, Council Post, May 15, 2023, 5 sheets, https://www.forbes.com/sites/forbestechcouncil/2023/05/15/journey-from-patient-outreach-to-meaningful-patient-engagement-how-behavioral-economics-may-help/?sh=5c22c99a1f23.

The Power of Large Behavior Models in Healthcare Consumer Engagement, Lirio Communication that moves people, JP Morgan Healthcare conference in San Francisco on Jan. 5, 2024, 10 sheets, https://lirio.com/blog/the-power-of-large-behavior-models-in-healthcare-consumer-engagement/.

"Machine Learning in Digital Patient Billing Services", Medium, MailMyStatements, Oct. 18, 2022, 9 sheets, https://mailmystatement.medium.com/machine-learning-in-digital-patient-billing-services-fc0c88eeda8a.

"AI and Automation in Medical Billing", Medical Billers and Coders, Oct. 20, 2023, 8 sheets, https://mailmystatement.medium.com/machine-learning-in-digital-patient-billing-services-fc0c88eeda8a.

* cited by examiner

ENGAGEMENT ENGINE ARCHITECTURE

CUSTOMER EXPERIENCE

CX LAYER

ENGAGEMENT
LEARNING ENGINE
FIG.2

AAW
SCORING
MODEL
FIG.2

NUDGE
MODULE
(BE)
FIG.2

LEARNING ENGINE

• USES PREDICTIONS, RECOMMENDATIONS, ANALYTICS TO RECOMMEND ACTIONS
• LEARNS FROM ACTION <> OUTCOMES RELATIONSHIPS
• HELPS WITH COHORTING PATIENTS

FIG. 2

DATA LAYER

EHR    PM    CREDIT SCORES    BIG DATA    SOCIAL ANALYTICS    CONSUMER BEHAVIOR

*FIG. 3*

NUDGE BANK-SAMPLES

| NUDGE CATEGORY | NUDGE DESCRIPTION | MEDIUM | AWARENESS SCORE | ABILITY SCORE | WILLINGNESS | ENGAGEMENT STAGE |
|---|---|---|---|---|---|---|
| EASE OF PAYMENT | SEND EZ PAYMENT LINK-PATIENT PORTAL | EMAIL, SMS | HIGH, MEDIUM | HIGH, MEDIUM | YES | PRE, INTRA, POST |
| EASE OF PAYMENT | OFFER OPTIONS TO PAY THRU: VENMO, ZELLE, GPAY, APPLE PAY, CASH APP | EMAIL, SMS | HIGH, MEDIUM | HIGH, MEDIUM | YES | PRE, INTRA, POST |
| EASE OF PAYMENT | OFFER EARLY PAYMENT DISCOUNT | EMAIL, SMS | HIGH, MEDIUM, LOW | MEDIUM, LOW | YES, NO | PRE, INTRA, POST |
| FINANCIAL ABILITY | OFFER PAYMENTS BY MONTHLY INSTALLMENTS | EMAIL, SMS | HIGH, MEDIUM, LOW | MEDIUM, LOW | YES | PRE, INTRA, POST |
| FINANCIAL ABILITY | OFFER PAYMENTS BY WEEKLY INSTALLMENTS | EMAIL, SMS | HIGH, MEDIUM, LOW | MEDIUM, LOW | YES | PRE, INTRA, POST |

*FIG. 4*

ENGAGEMENT LEARNING ENGINE

CROSS-REFERENCE TO RELATED APPLICATIONS

This application claims priority to U.S. Provisional Application Ser. No. 63/445,148, filed Feb. 13, 2023, the entire contents of which are hereby incorporated by reference in their entirety.

FIELD OF THE INVENTION

The present invention comprises a system and method for understanding and influencing behavioral drivers of key stakeholders to achieve predictable engagement outcomes in the healthcare industry (e.g., using an awareness, ability, and willingness (AAW) framework to reduce patient medical debt and improve collectability of patient share).

BACKGROUND

Most of the prevalent engagement solutions within healthcare today fail to deliver predictable and holistic engagement from the patients because they are solely focused on outreach instead of engagement. Patient engagement is a function of understanding their needs, awareness, ability and willingness to participate. Ability to text, email, and chat with the patient only generates outreach, which elicits what seems like early engagement but it fizzles out pretty quickly without any long term change in behavior. Another challenge with prevalent solutions is the generic nature of these engagement models which end up delivering generic content to the patients without understanding of their personalized needs and preferences. While some models use propensity to pay algorithms to predict likelihood of patients paying the outstanding bills, they are still vague, while effective in limited terms, do not holistically identify root cause driving the behavior and offer corrective long term solutions.

SUMMARY

Based on these limitations, a need clearly exists for a holistic engagement model deeply rooted in the principles of human psychology, behavioral economics and mathematical correlation after studying the behavior, attitude and preferences of patients. The AAW framework works by first identifying root causes that are causing lack of engagement and then uses the concept of behaviorally segmented 'Nudges' to deliver predictable engagement overtime. The AAW framework is preferably delivered using an artificial intelligence (AI) and machine learning (ML) technology platform to create personalized patient experience there by further enhancing and improving patient engagement. Further, the AI/ML model has cognitive learning abilities from the identified patterns, patient interactions and other inputs there by creating a perpetual loop of delivering precise nudges based on individual behaviors, outcomes delivered, interaction and other factors.

It is therefore an object of the present invention to provide an AAW framework that utilizes human psychology and behavioral economics to understand root causes of disengagement and create solutions that cater to identified needs.

Yet another object of the present invention is to provide personalized patient profiling based on individual preferences, behavior and attitudes.

Another object of the present invention is to utilize ML to create an infinite learning engine that updates itself based on the input from interactions, behaviors, and outcome seen.

It is another object of the present invention to provide personalized nudges to patients to increase engagement.

It should also be obvious to one skilled in the art that the engagement learning model of the present invention has applications to other common problems in healthcare such as medicine adherence and appointment no show predictions.

BRIEF DESCRIPTION OF THE DRAWINGS

FIG. 3 depicts a system diagram of the engagement learning engine architecture.

FIG. 4 depicts a plurality of sample nudges that may be provided to patients.

DETAILED DESCRIPTION

Figure 1:
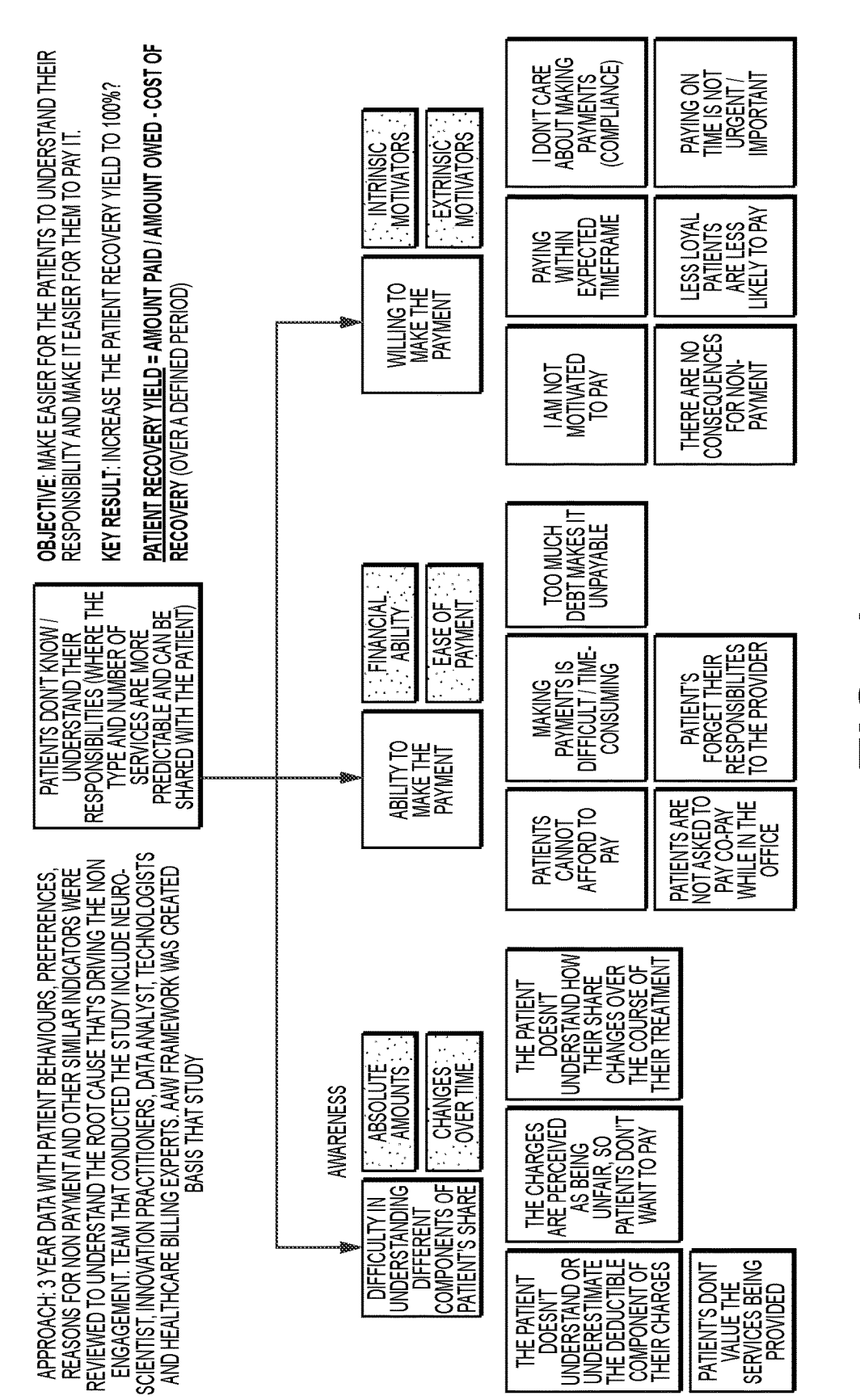
FIG. 1 depicts a flowchart showing root causes of why patients do not engage.

Referring first to FIG. 1, depicted is a flowchart showing likely root cause categories of why patients may not engage, especially with billing. Various aspects associated with patient behavior were analyzed to determine the root causes driving non-engagement. It was determined that the main causes for non-engagement were deficiencies in awareness, ability, and willingness (AAW). For example, many patients may have difficulty understanding different components of a bill and what their share is of the bill. Bills can often be confusing because they may detail absolute amounts or recurring charges within the same bill. Patient obligations, such as insurance deductibles, can also be difficult to understand.

Many patients may also lack the ability to make payments due to various circumstances such as current financial ability or inability to access different or obscure payment methods. The most basic reason patients may not pay is that they currently cannot afford payments due to a variety of circumstances. Other times making payments may be difficult or time consuming.

In certain circumstances, patients may simply be unwilling to make payments or may be lackadaisical/ambivalent, especially if the patient is occupied with other needs or payments (e.g., rent, mortgage, food, etc.). Patients that have not had a good experience are especially less likely to pay due to dissatisfaction. Understanding the various reasons for patient disengagement and/or non-payment allows the system of the present invention to provide "nudges" to patients which can help increase patient payments or at least better inform the patient as to their financial obligations related to any care they received.

Figure 2:
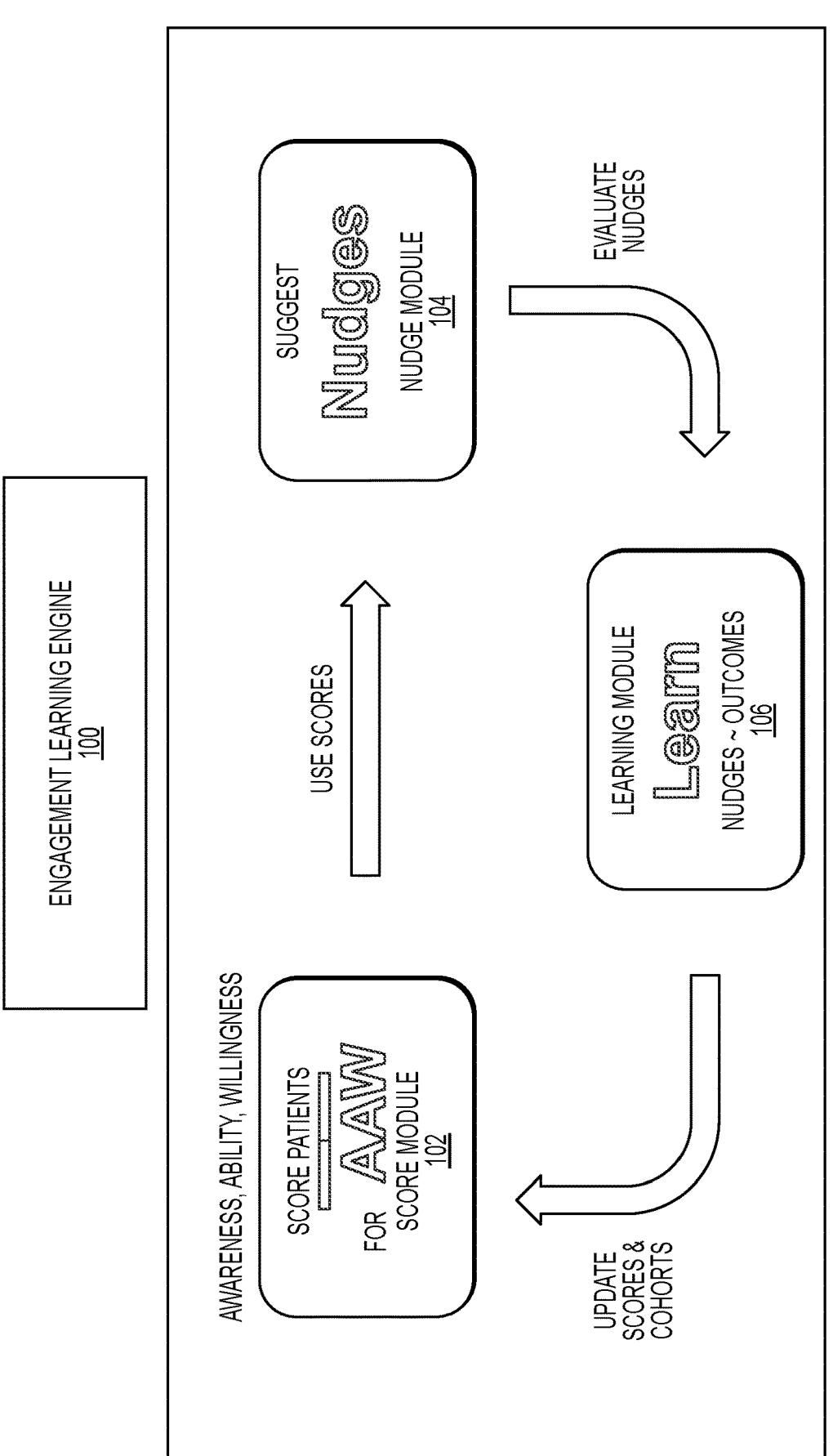
FIG. 2 depicts a system diagram of the engagement learning engine and its components.

Referring to FIG. 2, depicted is a system diagram showing the main components of the engagement learning engine 100, namely AAW score module 102, nudge module 104, and learning module 106. The engagement learning engine 100 calculates a score for each patient using AAW score module 102. The user score developed by the AAW score module 104 is utilized to select or develop one or more nudges that are provided to the patient. The responses from the patients to the nudges is utilized by learning module 106 to improve future feedback to the patients and to develop new or more effective nudges.

AAW Score Module

Practice Management data, Patient history, attributes, behavior, preferences, credit scores, social and consumer behavior data are used by the AAW score module 102 to score patients on the 3 dimensions—Awareness, Ability and Willingness. AAW scores inform which actions are picked in the nudge module 104, with the goal being to nudge users to maximize their AAW scores where possible.

Awareness Score

The AAW score module 102 may calculate one or more scores related to a patient's awareness. A simple awareness score may be indicated to first identify if the patient has acknowledged their current balance (either electronically or in person). If the patient has acknowledged their balance, a delta awareness score is calculated which is a proportion of overall patient balance that has been acknowledged. For example, if a patient now owes $100 but has acknowledged only $50, their awareness score is 0.50.

The AAW score module 102 may utilize an awareness formula to calculate the awareness score using the following equation $$\text{Awareness score} = Aam * Ar \tag{1}$$

Aam=Patient's awareness of the $ amount for which patient is responsible for the latest visit (yes: 1/no: 0).

Ar=Recency (measure of how recent in time) of when the patient was made aware of responsibility (decays exponentially over time).

Examples of the awareness score calculated using formula (1) are identified below:

Ability Score

The AAW score module 102 may utilize $3^{rd}$ party scores, such as credit scores, which judge a person's current financial ability to calculate the ability score. Other criteria that may be utilized include, but are not limited to, type of insurance, total balance paid, etc.

A simple awareness score can be calculated by the AAW score module by dividing the total patient responsibility over 12 months (or any time period) by the amount that has been paid. The AAW score module 102 may utilize an ability formula to calculate the awareness score using the following equation:

$$\text{Complex Ability score} = \text{Log}(Tr) * (1/Tr * Tp) \tag{2}$$

Tr=Total Responsibility over last 12 months.
Tp=Total Paid over last 12 months.
Examples of the ability score calculated using formula (2) are identified below:

| Patient ID | Total Responsibility over 12 months | Total Paid over 12 months | Ability Score (Complex) |
|---|---|---|---|
| 0 | $500.00 | $500.00 | 2.698970004 |
| 1 | $500.00 | $250.00 | 1.349485002 |
| 2 | $500.00 | $50.00 | 0.2698970004 |
| 3 | $5,000.00 | $5,000.00 | 3.698970004 |
| 4 | $5,000.00 | $2,500.00 | 1.849485002 |
| 5 | $5,000.00 | $500.00 | 0.3698970004 |

Willingness Score

| Patient ID | Last Event Date | Patient's awareness | Days Since last statement | Statement Score | Days Since last SMS | SMS score | Score using Euler's Number |
|---|---|---|---|---|---|---|---|
| 0 | Mar. 22, 2022 | TRUE | 235 | 0.009798234438 | 1 | 2.302585093 | 0.009799250466 |
| 1 | Mar. 31, 2022 | TRUE | 226 | 0.01018842962 | 4 | 0.5756462732 | 0.0101894861 |
| 2 | Apr. 10, 2022 | TRUE | 216 | 0.01066011617 | 22 | 0.1046629588 | 0.01066122157 |
| 3 | Apr. 20, 2022 | TRUE | 206 | 0.01117759754 | 30 | 0.07675283643 | 0.0111787566 |
| 4 | Oct. 13, 2022 | TRUE | 30 | 0.07675283643 | 4 | 0.5756462732 | 0.07676079532 |
| 5 | | FALSE | 0 | 0 | 0 | 0 | 0 |

In the table above, only recency of the last statement is used. However, additional testpoints may be used to identify additional scores. For example, different types of messaging or outreach may also be assigned a score (e.g., SMS score):

$$\text{Awareness score} = Aam * Ar * Af * Ac \tag{1.1}$$

Aam=We sent a digital message, did we got confirmation that they see the text? (0.1=not confirmed, 0.2=app notification 1=confirmed)

Ar=The last date the user was notify about a bill/number of days passed since then (function of time)

Ac=Reflects the effectiveness of communication channels used to inform the patient. (1=text message, 2=app notification, 3=mail, 4=email)

Af=How many time we notify the user for unpaid bills (1 notification=1, 2nd notification=1.2, 3rd notification=1.4)

Ac=Reflects the effectiveness of communication channels used to inform the patient. (1=text message, 2=app notification, 3=mail, 4=email)

The AAW score module 102 may calculate one or more scores related to a patient's willingness. An intrinsic willingness score may be calculated to indicate a proportion of outstanding balance paid that the patient was aware of, with a—greater proportion indicate higher scores. An extrinsic willingness score may be calculated to indicate a proportion of historical payments that required changes to service or payment collection services before payment.

The AAW score module 102 may utilize a willingness formula to calculate the awareness score using the following equation:

$$\text{Willingness score} = Ns * \text{DelayMin}(\text{SUM}(Pd)) \tag{3}$$

DelayMin=Minimum/average number of days needed by patients to receive and pay responsibility.

Pd=Payment delay—For the last 12 months—time in days between statement date and payment date, if Pd<DelayMin (1 week), round up to DelayMin.

Ns=Number of statements generated over last 12 Months.

The willingness score can be calculated for different time intervals (e.g., 3 months, 6 months, etc.). Examples of the willingness score calculated using formula (3) are identified below:

| Patient ID | Statement Date | Payment Date | Pd | Willingness score |
|---|---|---|---|---|
| 0 | Apr. 20, 2022 | Apr. 22, 2022 | 7 | |
| 0 | Mar. 20, 2022 | Mar. 25, 2022 | 7 | |
| 0 | Feb. 20, 2022 | Feb. 23, 2022 | 7 | 1 |
| 1 | Apr. 20, 2022 | NULL | 0 | |
| 1 | Mar. 20, 2022 | Apr. 19, 2022 | 30 | |
| 1 | Feb. 20, 2022 | Apr. 19, 2022 | 58 | 0.2386363636 |
| 2 | Apr. 20, 2022 | NULL | 0 | |
| 2 | Mar. 20, 2022 | NULL | 0 | |
| 2 | Feb. 20, 2022 | NULL | 0 | 0 |
| 3 | Jun. 1, 2022 | Jul. 1, 2022 | 30 | |
| 3 | Aug. 15, 2022 | Sep. 1, 2022 | 15 | |
| 3 | Oct. 15, 2022 | Oct. 15, 2022 | 1 | 0.45652174 |

$$\text{Willingness score} = Ah * \text{DelayMin} \qquad (3.1)$$

Ah=Number of statements that were paid in the last 12 months/Number of statements generated over last 12 months.

DelayMin–Minimum/average number of days needed by patients to receive and pay responsibility Patients' Benchmark Post calculations, the AAW score modules (102, 104, 106) will use a normalization data method to detect patients' underperformers, overperformers and the mean-performers in each category (awareness, ability, and willingness) according to the proportions of the collected scores. The scores in each category will be normalized to a range between [0,1]. This range of scores will allow the model to indicate whatever a patient is acting in the normal (x=0.5), below (x<0.5) or over (x>0.5) the scope of engagement found in the population. Moreover, it will allow the models to adjust to changes in patients' performance over time. In addition, a 3 level scale rating system (low, medium, and high) will be added to ranges [=>0,<0.5] and [>0.5,<=1] with the purpose of adding sensitivity indicators for the Nudge model detection consideration.

The AAW benchmark score module may utilize a formula to calculate the score using the following equation:

$$\text{Normalize score} = (xi - \min(x))/(\max(x) - \min(x))$$

where:
xi=data value
min(x)=minimum value in the dataset
max(x)=maximum value in the dataset The AAW benchmark sensitivity score will be calculated using the range of values from [0,1] for values < >0.5 as follow:

Values > 0.5(overperformers):

value[ > 0.5, = < 0.6666] = Low value[ > 0.6666, = < 0.8332] = Medium value[ > 0.8332, = < 1] = High Values < 0.5(underperformer):

value[ < 0.5, = > 0.3334] = Low value[ < 0.3334, = > 0.1668] = Medium value[ < 0.1668, = > 0] = High Example

| Patient ID | Total Responsibility over 12 months | Total Paid over 12 months | Ability Score (Complex) | Normalized score | Sensitivity |
|---|---|---|---|---|---|
| 0 | $500.00 | $500.00 | 2.698970004 | 0.7083 | overperformer (Medium) |
| 1 | $500.00 | $250.00 | 1.349485002 | 0.3148 | underperformer (Medium) |
| 2 | $500.00 | $50.00 | 0.2698970004 | 0 | underperformer (High) |
| 3 | $5,000.00 | $5,000.00 | 3.698970004 | 1 | overperformer (High) |
| 4 | $5,000.00 | $2,500.00 | 1.849485002 | 0.4606 | underperformer (Low) |
| 5 | $5,000.00 | $500.00 | 0.3698970004 | 0.0291 | underperformer (High) |

Nudge Module

The nudge module 104 provides feedback or suggestions to patients based upon the AAW score module 102 score and answers provided. The nudges provided to patients may be varied based on the type of care received, level of care, provider, etc. Generally, nudges are provided to directly address any reasons for non-engagement based on AAW. Awareness nudges may include:

Sending email/text message prior to appointment

Provider asking patient to acknowledge balance when scheduling future appointments Precompute and share potential outstanding balance for an entire episode of care Ability nudges may include:

Offering more channels of payment (e.g., Zelle, PayPal, Venmo)

Offer payment on different platforms such as smartphone, computer, tablet, phone, etc.

Willingness nudges may include:

Highlight pro-social messaging

90% of patients have paid their balance

Non-payment decreases the quality of care for all

Statistics on payments by others

Non-payment decreases the quality of care for all

Downgrade service till balances are paid

Personalized Willingness: Risk to collection referral

Mandatory payment before next visit-100% balance due before next visit

FIG. 4 depicts samples of nudges that may be provided to patients based on category and AAW criteria.

| Nudge Category | Nudge Description | Medium | Awareness Score | Ability Score | Willingness | Engagement Stage |
|---|---|---|---|---|---|---|
| Ease of Payment | Send EZ Payment Link - Patient Portal | Email, SMS | High, Medium | High, Medium | Yes | Pre, Intra, Post |
| Ease of Payment | Offer options to pay thru: Venmo, Zelle, Gpay, Apple Pay, Cash App | Email, SMS | High, Medium | High, Medium | Yes | Pre, Intra, Post |
| Ease of Payment | Offer Early Payment Discount | Email, SMS | High, Medium, Low | Medium, Low | Yes, No | Pre, Intra, Post |
| Financial Ability | Offer Payments by Monthly Installments | Email, SMS | High, Medium, Low | Medium, Low | Yes | Pre, Intra, Post |
| Financial Ability | Offer Payments by Weekly Installments | Email, SMS | High, Medium, Low | Medium, Low | Yes | Pre, Intra, Post |
| Personalized Willingness | Negative Framing + CTA - Collection referral impacts credit scores | Email, SMS | High, Medium, Low | Medium, Low | No | Intra, Post |
| Personalized Willingness | Negative Framing + CTA - You might be at risk of collection referral | Email, SMS | High, Medium, Low | Medium, Low | No | Intra, Post |
| Personalized Willingness | Positive Reinforcement - Offer access to concierge service | Email, SMS, App, Web | High, Medium, Low | Medium, Low | No | Intra, Post |
| Personalized Willingness | Positive Reinforcement - Offer to get an earlier appointment | Email, SMS, App, Web | High, Medium, Low | Medium, Low | No | Intra, Post |

Creation of AAW Keys

To map the Ability (A), Awareness (A), and Willingness (W) scores to the best suited nudge, AAW score ranges (high, medium, low) will be grouped into composite keys referred to as "AAW-Keys". There are 18 such combinations aka AAW-Keys that can be created based on individual AAW scores.

| AAW-Key | Ability | Awareness | Willingness |
|---|---|---|---|
| 1 | High | High | High |
| 2 | High | Medium | High |
| 3 | High | Low | High |
| 4 | High | High | Low |
| 5 | High | Medium | Low |
| 6 | High | Low | Low |
| 7 | Medium | High | High |
| 8 | Medium | Medium | High |
| 9 | Medium | Low | High |
| 10 | Medium | High | Low |
| 11 | Medium | Medium | Low |
| 12 | Medium | Low | Low |
| 13 | Low | High | High |
| 14 | Low | Medium | High |
| 15 | Low | Low | High |
| 16 | Low | High | Low |
| 17 | Low | Medium | Low |
| 18 | Low | Low | Low |

AAW-Nudge Mapping Model

Using the AAW_keys (described) above, a new data table will be created that will act as a X-Ref between AAW scores and Nudge Categories with user-experience based metadata. As a patient's AAW score is calculated, this Xref-table will be used to select the nudges. In the initial cycles, engagement channels, payment modes, etc. would be generically chosen. Subsequently, clustering algorithms will help with personalized patient engagement.

| AAW-Key | Nudge Category | Priority-Sequence | Journey | Nudge Execution Attributes |
|---|---|---|---|---|
| 1 | Ease of Payment | 1 | Post Visit | {Engagement Channel: Email; Language: English} |
| 1 | Financial Ability | 1 | Pre Visit | {Engagement Channel: Text; Language: English} |
| 2 | Personalized Willingness | 4 | Pre Visit | {Engagement Channel: Call; Language: Spanish; Payment mode: Hot link to patient portal} |

The nudge module 104 recommends actions, which are picked from a bank of possibilities for that provider. The actions are scored in the learning module 106 for their effect on the AAW scores to affect future cohorting of patients and actions selected. A ML based homogeneous clustering approach is deployed to create like clusters. AI models then engage patients based on their personalized preferences, historical behaviors and engagement propensity ascertained by the model.

Learning Module

A primary function of learning module 106 is to determine which nudges worked best for which patients and to alter future nudges based on the learned feedback, especially since not all nudges lead to the same outcome for each patient. The learning module 106 learns these patterns for each provider and their patients, learning which actions lead to better payment outcomes in that provider's patient population. Based on an AAW model, patients can be categorized into 6 different cohorts (e.g., High awareness+high ability+high willingness, and so on). The learning module 106 uses both pre-existing data and action outcome data to place patients into cohorts. This, in turn, helps determine which actions might be most useful in optimizing payments. In context, some cases of the difference between low to medium awareness and willingness agents, can be attributed to the failure of considering the "big picture" of a financial situation. For example, Imagine you had a cashback of $200 from your credit card company. Ordinarily, you're pretty good at paying your medical bills and you've been trying to budget some extra money for your family medical expenses. But, today you take your "new" $200 and put it towards a gift for your partner. You tell yourself that this money isn't for "medical coverage". This one is for a special gift. This kind of behavior is known as "mental accounting". Meaning, we tend to allocate money depending on how we acquire it, what is our intent of using it and how we feel about it. In this case, a typical nudge solution would be suggesting opening a FSA Health care account. The right allocation of financial resources towards health-care expenses and payments can have an important part in preventing future medical care debt. This AAW system will recognize these types of behaviors and use nudge methods to reduce them.

While specific embodiments of the invention have been described above, it will be appreciated that the invention may be practiced other than as described. The embodiment (s) described, and references in the specification to "one embodiment," "an embodiment," "an example embodiment," "some embodiments," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The description provided above is intended to be illustrative and non-limiting. Thus, it will be apparent to one skilled in the art that modifications may be made to the present invention as described. The above description may be naturally extended to other contexts.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described embodiments.

The invention claimed is:

1. A payment engagement system, having a processor, for encouraging payment of medical debt by patients, the engagement system comprising:
   a score module for calculating, using the processor, an engagement score based on primary feedback from a user related to the medical debt;
   a nudge module for automatically selecting, using the processor, at least one engagement nudge from a plurality of engagement nudges based on the engagement score and automatically transmitting the at least one engagement nudge to the a device of the user; and
   a learning module for monitoring secondary feedback to the at least one patient nudge by the user on the device and altering subsequent patient nudges delivered to the device based on the secondary feedback,
   wherein the engagement score comprises a debt awareness score, a payment ability score, and a payment willingness score,
   wherein the debt awareness score is calculated based on a number of days a most recent payment is outstanding,
   wherein the payment ability score is calculated as payment ability score=$\text{Log}(Tr)*(1/Tr*Tp)$, where $Tr$ is a total amount owed over a predetermined time period by the user and $Tp$ is a total amount paid over the predetermined time period by the user, and
   wherein the willingness score is calculated as willingness score=$Ns*\text{DelayMin}(\text{SUM}(Pd))$, where $Ns$ is a number of statements in the predetermined time period provided to the user, DelayMin is the average number of days to receive payment from the user related to the number of statements.

2. The payment engagement system according to claim 1 wherein the debt awareness score is calculated based on a number of days a most recent payment is outstanding.

3. The payment engagement system according to claim 1, wherein the awareness score, the ability score, and the willingness score are normalized before being combined to form the engagement score.

4. The payment engagement system according to claim 1, wherein the awareness score is assigned a first ranking, wherein the ability score is assigned a second ranking, and wherein the willingness score is assigned a third ranking.

5. The payment engagement system according to claim 4, wherein the nudge module selects the at least one engagement nudge based on the first ranking, the second ranking, or the third ranking.

6. The payment engagement system according to claim 4, wherein the first ranking is high, medium, or low.

\* \* \* \* \*